United States Patent [19]

McShane

[11] Patent Number: 4,515,719

[45] Date of Patent: May 7, 1985

[54] AZETIDINONE SULFINIC ACIDS FROM CEPHALOSPORIN SULFONES

[75] Inventor: Lawrence J. McShane, Indianapolis, Ind.

[73] Assignee: Eli Lilly and Company, Indianapolis, Ind.

[21] Appl. No.: 516,218

[22] Filed: Jul. 22, 1983

[51] Int. Cl.[3] ............... C07D 205/08; C07D 501/14; C07D 403/12

[52] U.S. Cl. ............. 260/239 A; 260/245.4; 544/17

[58] Field of Search ......... 260/245.4, 239 A

[56] References Cited

U.S. PATENT DOCUMENTS 4,159,266 6/1979 Kukolja ............ 260/239 A 4,368,156 1/1983 Spitzer et al. ............ 260/239 A

OTHER PUBLICATIONS

C. M. Pant and R. J. Stoodley, *J.C.S. Perkin I.*, 1978, pp. 1366–1369.

U.S. application Ser. No. 442,075 filed 11/16/82, David A. Hall.

*Primary Examiner*—Mark L. Berch
*Attorney, Agent, or Firm*—Charles W. Ashbrook; Arthur R. Whale

[57] ABSTRACT

3-Exomethylene cepham sulfones are converted to azetidinone sulfinic acids by reaction with activated zinc, magnesium, activated magnesium or amalgamated magnesium and a protonic acid.

4 Claims, No Drawings

AZETIDINONE SULFINIC ACIDS FROM CEPHALOSPORIN SULFONES

BACKGROUND OF THE INVENTION

This invention concerns a process for converting 3-exomethylene cepham sulfones to azetidinone sulfinic acids that are useful in the synthesis of 1-oxadethiacephalosporin antibiotics.

A new class of antibiotics recently has been discovered whose members have proven to be very effective against a broad spectrum of bacterial infections. This new class of compounds is defined as the 1-oxadethiacephalosporins, and is characterized as cephalosporin analogs having an oxygen atom in place of the sulfur atom in the cephalosporin nucleus. This new class of compounds is discussed by Sheehan et al. in *J. Heterocyclic Chemistry*, Vol. 5, page 779 (1968); Christensen et al, in *J. Am. Chem. Soc.* Vol. 96, page 7582 (1974); and Narisada et al., U.S. Pat. No. 4,138,486.

The reported synthesis of 1-oxadethiacephalosporins have employed, inter alia, haloazetidinones such as 4-chloroazetidinones; see U.S. Pat. Nos. 4,013,653, 4,234,724 and 4,159,984. These haloazetidinone starting materials generally have been prepared by reaction of a penicillin with a halogenating agent such as molecular halogen or an N-halo succinimide, U.S. Pat. No. 4,159,984. Narisada et al., in U.S. Pat. No. 438,486, described the synthesis of chloroazetidinones from methylthioazetidinones, which in turn are derived from penicillins. To date, haloazetidinones have not been available from cephalosporin starting materials.

An object of this invention is to provide a chemical process for converting cephalosporin sulfones to azetidinone sulfinic acids that in turn can be converted to haloazetidinones, which are then converted to 1-oxadethiacephalosporin antibiotics.

BACKGROUND OF THE INVENTION

This invention provides a process for converting certain cephalosporin sulfones to azetidinone sulfinic acids. The invention more particularly provides a process for preparing an azetidinone sulfinic acid of the formula

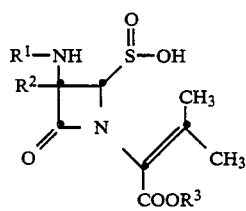

wherein $R^1$ is an acyl residue of a carboxylic acid, $R^2$ is hydrogen, lower alkoxy or lower alkylthio, and $R^3$ is a removable ester forming group; which process comprises reacting a 3-exomethylene sulfone of the formula

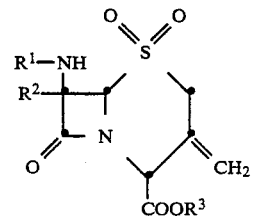

with activated zinc, magnesium, activated magnesium, or amalgamated magnesium and a protonic acid in an unreactive solvent at a temperature of about 20° to about 100° C.

The process is preferably carried out employing a protonic acid that is, for instance, bound to an amine compound. A particularly preferred bound protonic acid is ammonium chloride.

Another preferred embodiment is to carry the process out on a sulfone of the above formula wherein $R^1$ is

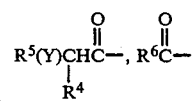

wherein:

$R^4$ is hydrogen, amino, protected amino, hydroxy, protected hydroxy, tetrazolyl, carboxy, or protected carboxy;

$R^5$ is hydrogen, phenyl, substituted phenyl, cyclohexadienyl, or a 5- or 6-membered monocyclic heterocyclic ring containing one or more oxygen, sulfur or nitrogen heteroatoms in the ring, said ring being substituted with hydrogen or amino;

Y is oxygen or a direct link; and $R^6$ is hydrogen, phenyl, substituted phenyl, alkyl or substituted alkyl.

The process is conveniently carried out employing 3-exomethylene cepham sulfone substrates wherein $R^1$ is

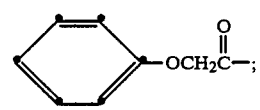

(a)

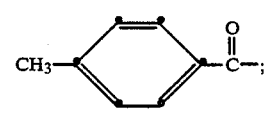

(b)

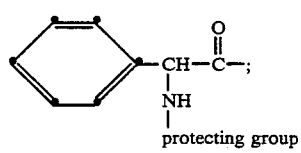

(c)

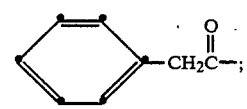

(d)

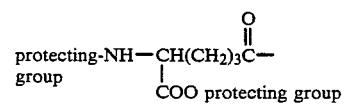

(e)

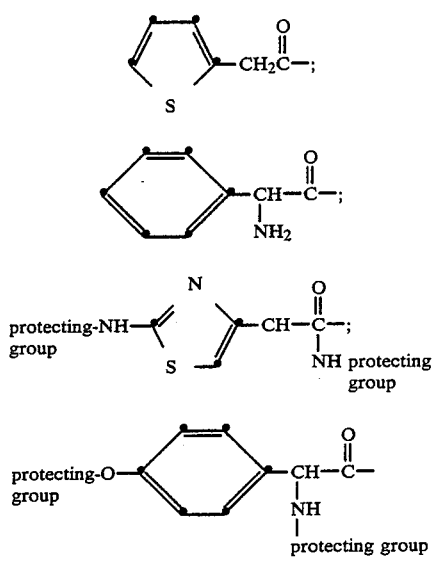

A preferred metal to be employed in the process of this invention is activated zinc. Preferred reaction solvents to be employed include N,N-dimethylformamide.

DETAILED DESCRIPTION OF THE INVENTION $R^1$ in the above formulas defines an acyl residue of a carboxylic acid. Since the process of this invention operates on the ring nucleus of the cephalosporin starting material, the particular $R^1$ group attached to the 7-amino group of the substrate is not critical to the process. Numerous and varied acyl residues of carboxylic acids are known in the cephalosporin and penicillin arts, and all such groups are contemplated by this invention. U.S. Pat. Nos. 4,052,387 and 4,243,588 disclose representative and typical carboxylic acid acyl residues, and these references are incorporated herein for those teachings.

Preferred cephalosporin sulfones to be employed in the present process include those defined by the above formula wherein $R^1$ is

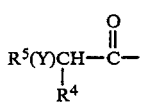

in which Y is oxygen or a direct link, $R^4$ is hydrogen, amino, protected amino, hydroxy, protected hydroxy, tetrazolyl, carboxy or protected carboxy; and $R^5$ is hydrogen, phenyl, substituted phenyl, cyclohexadienyl, or a 5 or 6-membered heterocyclic ring. As used herein, the terms "protected amino," "protected hydroxy," and "protected carboxy" have their respective art recognized meanings. For instance, "protected amino" means an amino group that has been derivatized with a readily cleavable group that is capable of preventing unwanted side reactions of the amino group during the course of the present process, or alternatively aid in solubilizing the amino containing substrate. Groups that are employed as protecting groups for amino, hydroxy and carboxy moieties are well known, and many are exemplified in Chapters 2, 3 and 5 of *Protective Groups in Organic Chemistry*, Plenum Press, New York, N.Y., 1973.

Typical amino protecting groups include tert.-butoxycarbonyl, benzyloxycarbonyl, 4-methoxybenzyloxycarbonyl, 4-nitrobenzyloxycarbonyl, and the 1-carbomethoxy-2propenyl group. Commonly used hydroxy protecting groups include acyl groups such as formyl, acetyl, chloroacetyl; arylalky groups such as benzyl and 4-nitrobenzyl, and alkyl groups such as methoxymethyl and tert.-butyl. Groups routinely employed to protect carboxy groups, and that constitute what are referred to herein as "removable ester forming groups," include alkyl groups such as methyl, tert.-butyl, $C_2$-$C_6$ alkanoyloxymethyl and the like, and arylalkyl groups such as diphenylmethyl, benzyl, 4-methoxybenzyl, 4-nitrobenzyl, tri($C_1$-$C_3$ alkyl)silyl, succinimidomethyl, and related groups. When reference is made herein to hydroxy, amino or carboxy groups, the respective protected groups are also contemplated. All that is intended is that such groups can be substituted with conventional blocking groups used for the temporary protection of such groups against undesired side reactions, and to aid in solublization of the compound containing such protecting groups. Such protected groups can be converted to the corresponding free hydroxy, carboxy or amino group by conventional methods.

The term "substituted phenyl" means a phenyl group bearing one or two substituents selected from lower alkyl, for instance, $C_1$-$C_4$ alkyl, amino, hydroxy or lower alkoxy.

Exemplary carboxylic acid acyl residues defined by

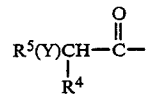

include phenylacetyl, phenoxyacetyl, 4-cyanophenylacetyl, 4-tert.-butoxyphenylacetyl, α-hydroxyphenylacetyl, α-aminophenylacetyl, α-tert.-butoxycarbonylaminophenylacetyl, α-ethoxycarbonylphenylacetyl, 4-nitrophenoxyacetyl and the like.

Another preferred $R^1$ carboxylic acid acyl residue is defined by

where $R^6$ is hydrogen, alkyl, for example $C_1$-$C_6$ alkyl, phenyl, substituted phenyl or substituted alkyl. Ther term "substituted alkyl" includes a $C_1$-$C_6$ alkyl group bearing one or more substituents such as hydroxy, amino, carboxy, or alkoxy. Exemplary

groups include formyl, acetyl, n-butyryl, 5-aminopentanoyl, benzoyl, 4-aminobenzoyl, 3-hydroxybenzoyl, 4-methylbenzoyl, and 2,6-diethylbenzoyl.

According to the process of this invention, a 3-exomethylene-1,1-dioxocepham, i.e., a cephalosporin sulfone, is reacted with a metal such as activated zinc, activated magnesium, magnesium, or amalgamated magnesium, and a protonic acid, to provide an azetidinone-4-sulfinic acid. A preferred metal to be employed in the process is activated zinc. Activated zinc is simply zinc metal that is substantially free of oxide coatings. Zinc metal dust that is commercially available generally has one or more layers of zinc oxide coating. These are readily removed by simply washing the zinc with a dilute mineral acid, for example 1N hydrochloride acid or 1N sulfuric acid. The activated metal that is thus formed generally is washed with a solvent that is to be employed in the process of the invention, although any common laboratory solvent can be employed. Typical solvents to be employed in the instant process are the polar solvents such as N,N-dimethylformamide, formamide, dimethyl sulfoxide, hexamethylphosphortriamide, or N,N-dimethylacetamide. Less polar organic solvents can be employed if desired, for example alcohols such as methanol, ethanol, isopropanol, as well as ethers such as diethyl ether, methyl ethyl ether, tetrahydrofuran, and ketones such as acetone or methyl ethyl ketone. A preferred solvent for the process is N,N-dimethylformamide. If desired, more than one solvent can be employed, and a mixture of N,N-dimethylformamide and water in a volume ratio of about 80:20 is a particularly preferred solvent system.

The process of the invention is carried out in the presence of a protonic acid, and any number of common protonic acids can be utilized. Typical protonic acids commonly employed include the mineral acids such as hydrochloric acid, hydrobromic acid, sulfuric acid, nitric acid, phosphoric acid, as well as organic protonic acids such as formic acid, acetic acid, trifluoroacetic acid, chloroacetic acid, methanesulfonic acid, benzoic acid, and the like.

If desired, the protonic acid can be employed in the form of a bound proton source, for example in the form of an amine acid addition salt. Typical amines commonly used to bind the protonic acid include ammonia and lower alkyl amines such as methyl amine, dimethyl amines, triethyl amine, as well as cyclic and aromatic amines such as pyrrolidine, piperizine, pyridine and the like. Ammonia is an especially preferred amine to be employed, and hydrochloric acid is a preferred protonic acid to be used in conjunction with ammonia (i.e., ammonium chloride).

While the respective quantities of metal and protonic acid to be employed in the process are not critical, it is preferred to use about an equimolar or excessive quantity of each in order to promote complete conversion of the 3-exomethylene cephalosporin sulfone. An amount of metal and acid ranging from about 1 to about 50 molar excess relative to the cepham sulfone starting material is routinely employed, although larger or smaller excesses are not detrimental and can be utilized if desired.

The reaction of the 3-exomethylene sulfone, the metal and the protonic acid generally is carried out at a temperature of about 20° to about 100° C., and more typically at about 25° to about 60° C. The reaction generally is substantially complete after about 2 to about 24 hours when carried out within this temperature range.

The product of the present process, an azetidinone-4-sulfinic acid, is readily isolated if desired by routine procedures. For example, the reaction mixture can be filtered to remove any excess metal, and the filtrate can be concentrated to dryness. The product thus formed can be further purified if needed by routine methods including salt formation and crystallization. The product of the process is most conveniently not isolated, but rather is simply reacted further in situ with a halogenating agent such as N-chlorosuccinimide or N-bromosuccinimide in order to obtain a 4-haloazetidinone of the formula

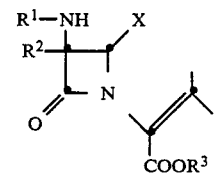

wherein $R^1$, $R^2$ and $R^3$ are as defined above, and X is halo such as fluoro, chloro, bromo or iodo. Such haloazetidinones are useful in the synthesis of 1-oxadethiacephalosporin compounds that are either active as antibiotics or are readily convertable to antibiotics, for example by removing any protecting groups or the like. The conversion of haloazetidinones to 1-oxadethiacephalosporins is described in U.S. Pat. Nos. 4,013,653 and 4,234,724.

The process of this invention operates equally well on cepham sulfones wherein the 7-acylamido side chain is in the natural or $\beta$-configuration, or wherein the 7-acylamido side chain is in the $\alpha$- or epi configuration. The configuration of the acylamido group is maintained throughout the process so that the azetidinone-4-sulfinic acid produced has an acylamido side chain in the same configuration as the starting material employed. Accordingly, there are produced by the present process natural azetidinone-4-sulfinic acids of the formula

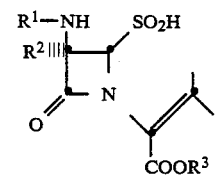

and epi-azetidinone-4-sulfinic acids of the formula

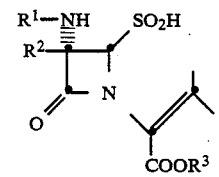

The process of this invention is more fully described by the following working examples.

EXAMPLE 1

Diphenylmethyl 3-methyl-2-(2-sulfinyl-4-oxo-3-(4-methylbenzoylamino)-1-azetidinyl)-2-butenoate A suspension of 3.18 g (6 mM) of diphenylmethyl 7-$\beta$-(4-methylphenylcarboxamido)-3-exomethylenecepham-1,1-dioxide-4-carboxylate in 35 ml of N,N-dimethylformamide and 5 ml of water was stirred at 25° C. under a nitrogen blanket. Six grams of ammonium chloride were added in one portion to the reaction mixture, followed by the addition of 7.5 g of zinc metal dust that had been washed with 50 ml of 1N hydrochloric acid. The reaction mixture was stirred for twenty-four hours at 25° C., and then filtered through hyflo filter aid. The filter cake was washed with 20 ml of N,N-dimethylformamide and then with 200 ml of ethyl acetate. The filtrate was washed three times with 100 ml portions of 5% (v/v) aqueous hydrochloric acid. The organic layer was separated, washed with brine, dried, and the solvent was removed by evaporation under reduced pressure to give 3.5 g of a white foam identified as diphenylmethyl 3-methyl-2-(2-sulfinyl-4-oxo-3-(4-methylbenzoylamino)-1-azetidinyl)-2-butenoate.

IR(CHCl$_3$): 1778 cm$^{-1}$.

NMR (CDCl$_3$): δ2.01–2.25 (three singlets, 3H each); δ4.70 (d, 1H); δ5.60 (dd, 1H); δ6.1–7.9 (m, 16H); δ9.35 (s, 1H).

EXAMPLE 2

Diphenylmethyl 3-methyl-2-(2-sodium sulfonyl-4-oxo-3-(4-methylbenzoylamino)-1-azetidinyl)-2-butenoate To a stirred suspension of 3.18 g (6 mM) of diphenylmethyl 7-β-(4-methylphenylcarboxamido)-3-exomethylenecepham-1,1-dioxide-4-carboxylate in 35 ml of N,N-dimethylformamide and 5 ml of water were added 6.0 g of ammonium chloride followed by addition of 7.5 g of activated zinc (activated by washing twice with dilute hydrochloric acid and twice with water). The reaction mixture was stirred at 25° C. for twenty-four hours under a nitrogen blanket. The reaction mixture was filtered through hyflo filter aid, and the filter cake was washed with 100 ml of ethyl acetate. The filtrate was washed with 5% aqueous hydrochloric acid and dried. The solution was stirred while a solution of 1 g (6 mM) of sodium 2-ethylhexanoate in 20 ml of ethyl acetate was added in one portion. The reaction mixture was stirred at 25° C. for sixteen hours, and then the solvent was removed by evaporation under reduced pressure to provide an oil. The oil was crystallized from 50 ml of chloroform to afford 1.0 g of diphenylmethyl 3-methyl-2-(sodium sulfonyl-4-oxo-3-(4-methylbenzoylamino)-1-azetidinyl)-2-butenoate of the formula

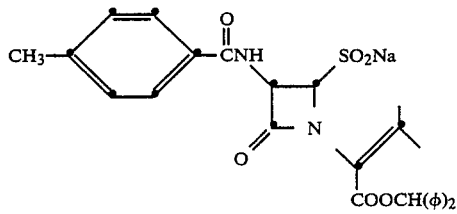

IR (KBr): 1776 cm$^{-1}$.

NMR (DMSOd$_6$): δ2.05 (s, 3H); δ2.18 (s, 3H); δ2.39 (s, 3H); δ4.56 (d, 1H); δ5.56 (dd, 1H); δ7.3–7.5 (m, 13H); δ7.70 (d, 2H); δ8.71 (d, 1H).

EXAMPLE 3

Benzyl 3-methyl-2-[2-sulfinyl-4-oxo-3-methoxy-3-(phenylacetamido]-1-azetidinyl)-2-butenoate A solution comprised of 2.5 g (5.15 mM) of benzyl 7-β-(phenylacetamido)-7-α-methoxy-3-exomethylenecepham-1,1-dioxide-4-carboxylate in 20 ml of DMF and 75 ml of ethanol was heated to 65° C. and stirred while 8.25 g (154.79 mM) of ammonium chloride were added in one portion, followed by the addition of 16.83 g (257.5 mM) of activated zinc. The reaction mixture was stirred for three hours at 65° C. and then cooled to about 30° C. The reaction mixture was diluted by addition of 100 ml of ethyl acetate, and the mixture was washed six times with 20 ml portions of 1N hydrochloric acid and once with brine. The organic solution was dried and concentrated to dryness to provide benzyl 3-methyl-2-[2-sulfinyl-4-oxo-3-methoxy-3-(phenylacetamido]-1-azetidinyl]-2-butenoate.

I claim:

1. A process for preparing an azetidinone sulfinic acid of the formula

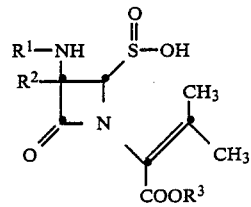

wherein:
R$^1$ is an acyl residue of a carboxylic acid;
R$^2$ is hydrogen, lower alkoxy or lower alkylthio; and
R$^3$ is a removable ester forming group; comprising reacting a 3-exomethylene sulfone of the formula

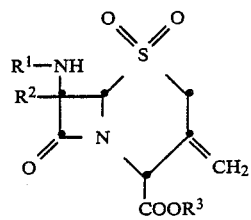

with activated zinc, magnesium, activated magnesium or magnesium amalgamated with mercury and a protonic acid in an unreactive solvent at a temperature of about 20° to about 100° C.

2. The process according to claim 1 employing N,N-dimethylformamide as reaction solvent.

3. The process according to claim 1 employing a substrate wherein R$^1$ is

4. The process according to claim 1 employing activated zinc.